(12) United States Patent
Zhu

(10) Patent No.: US 9,700,725 B2
(45) Date of Patent: *Jul. 11, 2017

(54) NEUROMODULATION USING MODULATED PULSE TRAIN

(71) Applicant: Boston Scientific Neuromodulation Corporation, Valencia, CA (US)

(72) Inventor: Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/920,229

(22) Filed: Oct. 22, 2015

(65) Prior Publication Data

US 2016/0106985 A1   Apr. 21, 2016

Related U.S. Application Data

(63) Continuation of application No. 14/195,632, filed on Mar. 3, 2014, now Pat. No. 9,174,053.

(Continued)

(51) Int. Cl.
*A61N 1/00* (2006.01)
*A61N 1/36* (2006.01)
*A61N 1/372* (2006.01)

(52) U.S. Cl.
CPC ..... *A61N 1/36178* (2013.01); *A61N 1/36071* (2013.01); *A61N 1/36189* (2013.01);
(Continued)

(58) Field of Classification Search
CPC ............ A61N 1/36071; A61N 1/36178; A61N 1/37247; A61N 1/36189; A61N 1/36192; A61N 1/36196
See application file for complete search history.

(56) References Cited

U.S. PATENT DOCUMENTS

| 4,338,945 A | 7/1982 | Kosugi et al. |
| 5,782,874 A | 7/1998 | Loos |

(Continued)

FOREIGN PATENT DOCUMENTS

| CN | 201139869 Y | 10/2008 |
| WO | WO-2016191055 A1 | 8/2015 |
| WO | WO-2016191055 A1 | 12/2016 |

OTHER PUBLICATIONS

"U.S. Appl. No. 14/195,632, Non Final Office Action mailed Mar. 18, 2015", 6 pgs.

(Continued)

*Primary Examiner* — George Manuel
(74) *Attorney, Agent, or Firm* — Schwegman Lundberg & Woessner, P.A.

(57) ABSTRACT

A neuromodulation system comprises a plurality of electrical terminals configured for being respectively coupled to a plurality of electrodes, a user interface configured for receiving input from a user that selects one of a plurality of different shapes of a modulating signal and/or selects one of a plurality of different electrical pulse parameters of an electrical pulse train, neuromodulation output circuitry configured for outputting an electrical pulse train to the plurality of electrical terminals, and pulse train modulation circuitry configured for modulating the electrical pulse train in accordance with the selected shape of the modulating signal and/or selected electrical pulse parameter of the electrical pulse train.

20 Claims, 17 Drawing Sheets

Related U.S. Application Data

(60) Provisional application No. 61/774,835, filed on Mar. 8, 2013.

(52) U.S. Cl.
CPC ...... *A61N 1/37247* (2013.01); *A61N 1/36192* (2013.01); *A61N 1/36196* (2013.01)

(56) References Cited

U.S. PATENT DOCUMENTS

| | | | |
|---|---|---|---|
| 6,246,912 B1 | 6/2001 | Sluijter et al. | |
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 7,076,307 B2 * | 7/2006 | Boveja | A61N 1/08 607/45 |
| 7,539,538 B2 | 5/2009 | Parramon et al. | |
| 8,010,198 B2 | 8/2011 | Libbus et al. | |
| 8,036,754 B2 | 10/2011 | Lee et al. | |
| 8,175,705 B2 | 5/2012 | Libbus | |
| 8,249,711 B2 | 8/2012 | Libbus et al. | |
| 8,401,653 B2 | 3/2013 | Libbus et al. | |
| 8,644,947 B2 | 2/2014 | Zhu et al. | |
| 8,694,104 B2 | 4/2014 | Libbus et al. | |
| 8,706,250 B2 | 4/2014 | Zhu et al. | |
| 8,788,048 B2 | 7/2014 | Bennett et al. | |
| 8,788,054 B2 | 7/2014 | Kothandaraman et al. | |
| 8,909,350 B2 | 12/2014 | Lee | |
| 9,138,582 B2 | 9/2015 | Doan et al. | |
| 9,174,053 B2 | 11/2015 | Zhu | |
| 9,238,138 B2 | 1/2016 | Lee et al. | |
| 2002/0143365 A1 | 10/2002 | Herbst | |
| 2003/0139781 A1 | 7/2003 | Bradley et al. | |
| 2004/0267333 A1 | 12/2004 | Kronberg | |
| 2005/0267546 A1 | 12/2005 | Parramon et al. | |
| 2006/0149337 A1 | 7/2006 | John | |
| 2007/0027486 A1 | 2/2007 | Armstrong | |
| 2007/0142874 A1 | 6/2007 | John | |
| 2008/0243204 A1 | 10/2008 | Uthman et al. | |
| 2009/0024189 A1 | 1/2009 | Lee et al. | |
| 2010/0274314 A1 | 10/2010 | Alataris et al. | |
| 2011/0009923 A1 | 1/2011 | Lee | |
| 2012/0215279 A1 | 8/2012 | Libbus | |
| 2013/0131760 A1 | 5/2013 | Rao et al. | |
| 2013/0304152 A1 | 11/2013 | Bradley et al. | |
| 2014/0088674 A1 | 3/2014 | Bradley | |
| 2014/0222100 A1 | 8/2014 | Libbus et al. | |
| 2014/0243925 A1 | 8/2014 | Kothandaraman | |
| 2014/0257428 A1 | 9/2014 | Zhu | |
| 2014/0364920 A1 | 12/2014 | Doan et al. | |
| 2014/0364921 A1 | 12/2014 | Legay et al. | |
| 2016/0001087 A1 | 1/2016 | Moffitt | |
| 2016/0129247 A1 | 5/2016 | Lee et al. | |
| 2016/0279422 A1 | 9/2016 | Libbus et al. | |
| 2016/0346546 A1 | 12/2016 | Zhu | |

OTHER PUBLICATIONS

"U.S. Appl. No. 14/195,632, Notice of Allowance mailed Jun. 26, 2015", 5 pgs.

"U.S. Appl. No. 14/195,632, Response filed Jun. 18, 2015 to Non Final Office Action mailed Mar. 18, 2015", 10 pgs.

Que, Doan T, et al., "Multi-Channel Neuromodulation System Having Frequency Modulation Stimulation", U.S. Appl. No. 61/768,286, filed Feb. 22, 2013.

Libbus, Imad, et al., "System for Providing Stimulation Pattern to Modulate Neural Activity", U.S. Appl. No. 15/083,011, filed Mar. 28, 2016.

Zhu, Changfang, "Neuromodulation Using Stochastically-Modulated Stimulation Parameters", U.S. Appl. No. 15/146,145, filed May 4, 2016.

\* cited by examiner

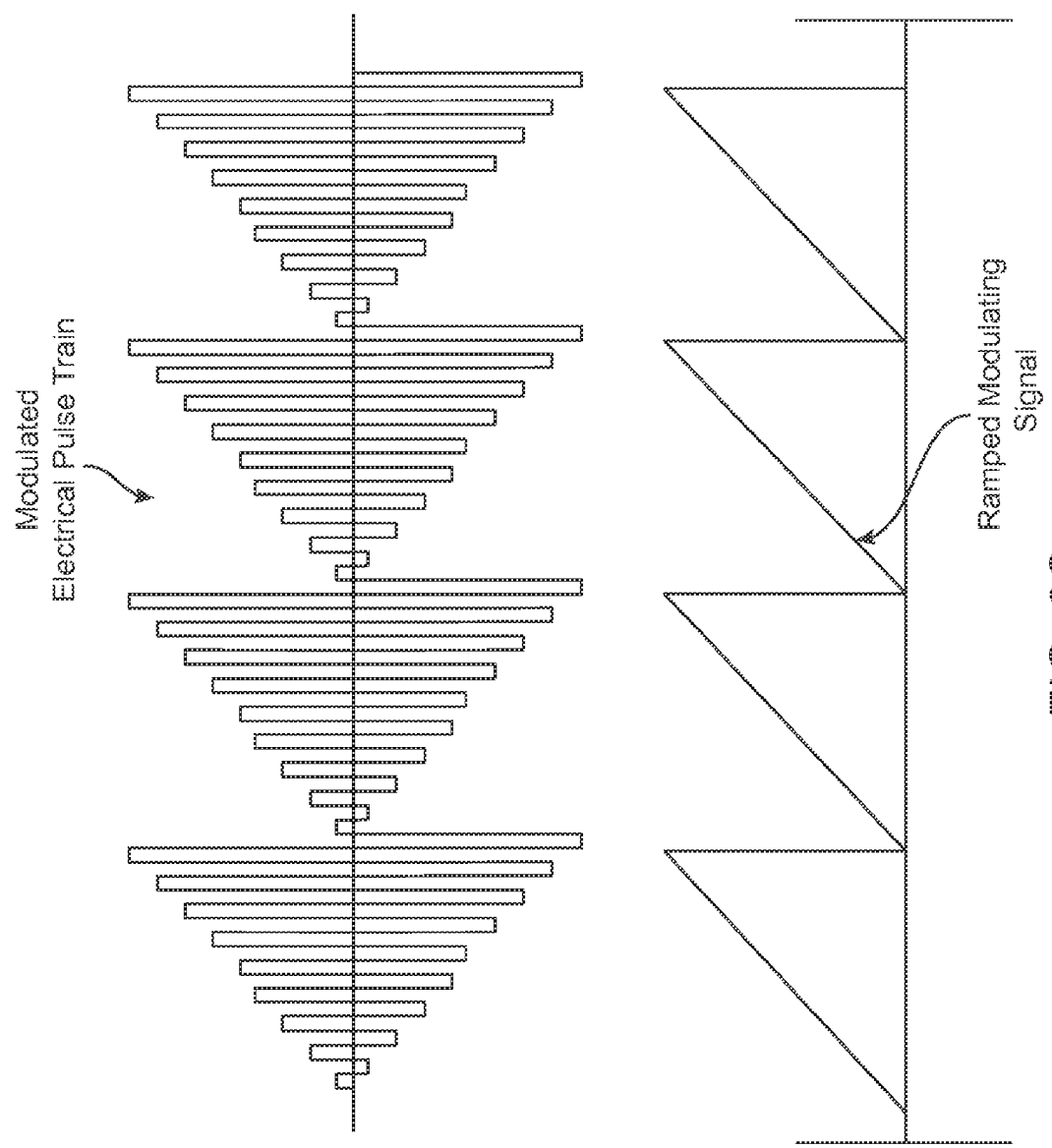

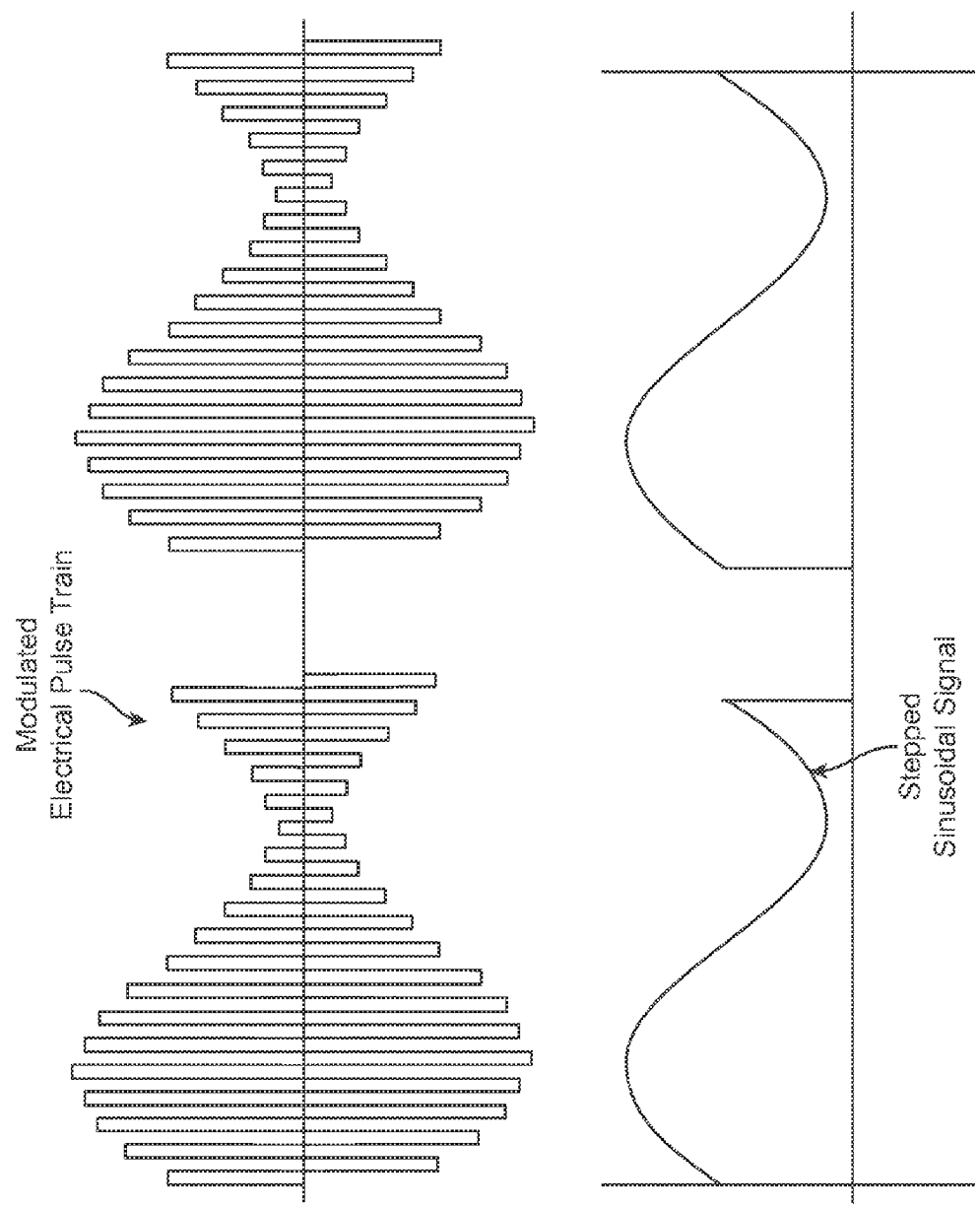

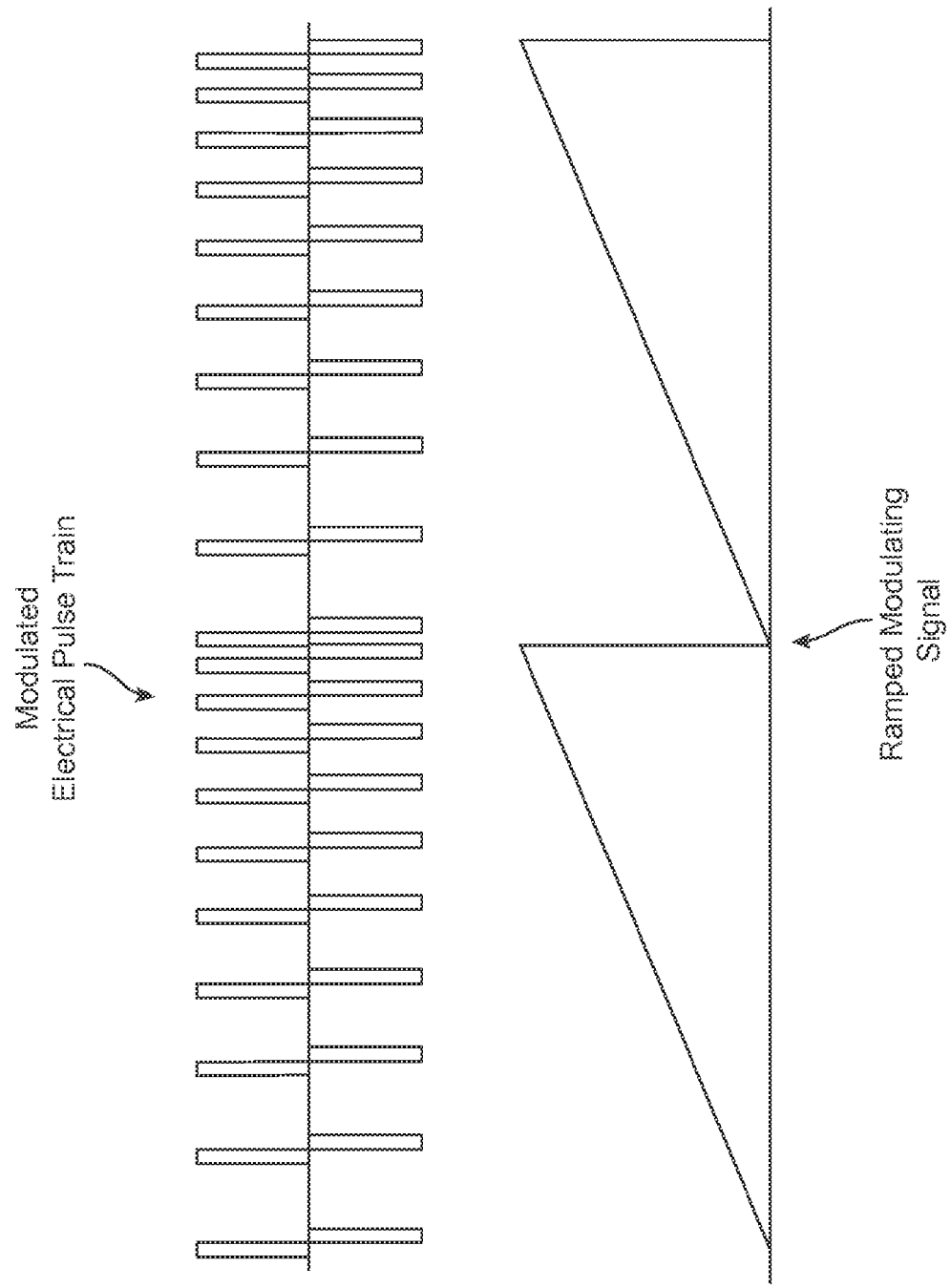

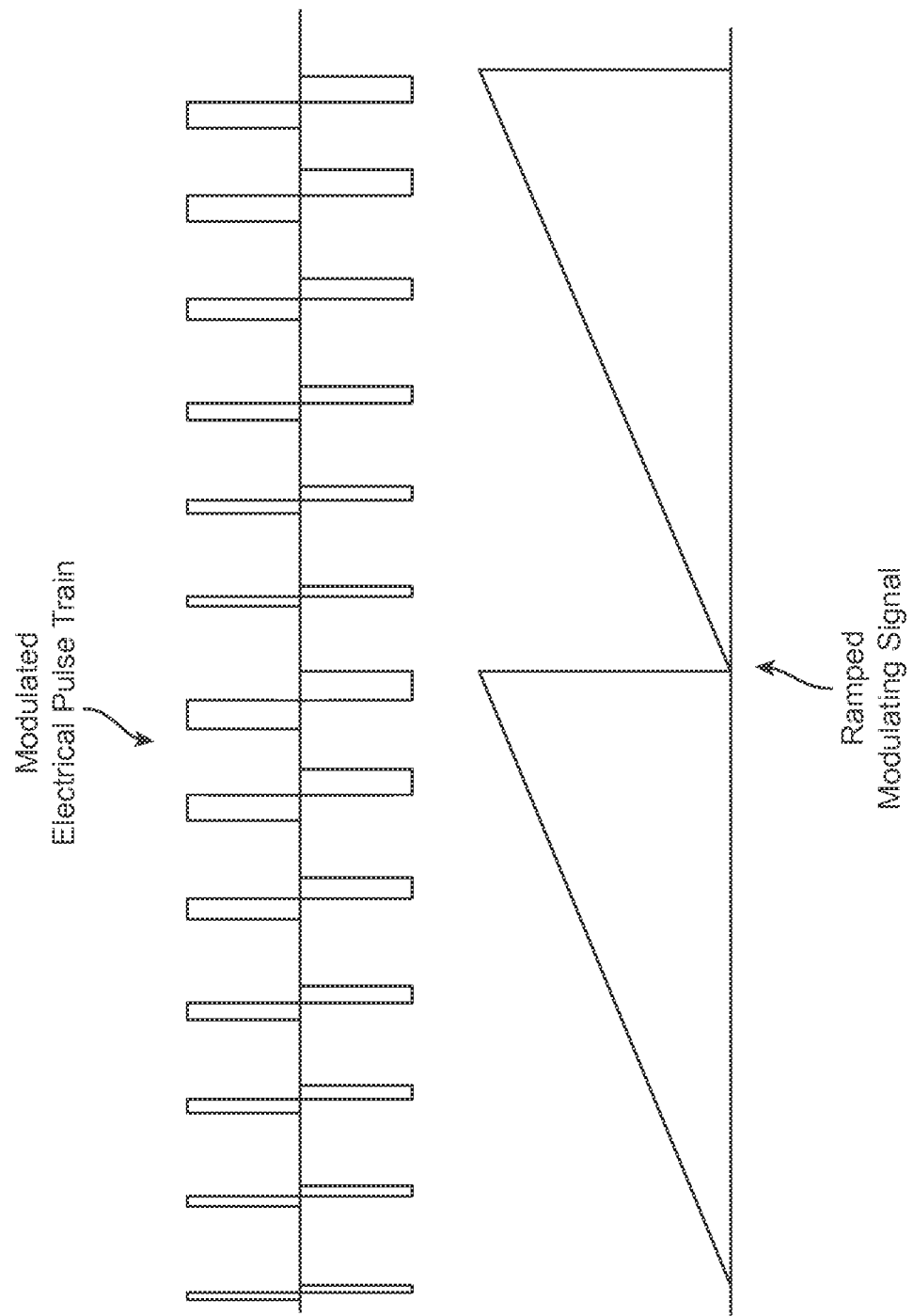

NEUROMODULATION USING MODULATED PULSE TRAIN

RELATED APPLICATION DATA

The present application is a continuation of U.S. application Ser. No. 14/195,632, filed Mar. 3, 2014, now issued as U.S. Pat. No. 9,174,053, which claims the benefit under 35 U.S.C. §119 to U.S. provisional patent application Ser. No. 61/774,835, filed Mar. 8, 2013. The foregoing applications are hereby incorporated by reference into the present application in their entirety.

FIELD OF THE INVENTION

The present invention relates to neuromodulation systems, and more particularly, to neuromodulation system utilizing electrical pulse trains.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neuromodulation systems typically include one or more electrode carrying modulation leads, which are implanted at the desired stimulation site, and a neuromodulator (e.g., an implantable pulse generator (IPG)) implanted remotely from the stimulation site, but coupled either directly to the neuromodulation lead(s) or indirectly to the neuromodulation lead(s) via a lead extension. The neuromodulation system may further comprise a handheld patient programmer to remotely instruct the neuromodulator to generate electrical stimulation pulses in accordance with selected stimulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

Electrical modulation energy may be delivered from the neuromodulator to the electrodes in the form of a pulsed electrical waveform. Thus, modulation energy may be controllably delivered to the electrodes to modulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, duration, and rate of the electrical pulses provided through the electrode array. Each electrode combination, along with the electrical pulse parameters, can be referred to as a "neuromodulation parameter set."

Of course, neuromodulators are active devices requiring energy for operation, and thus, the neurostimulation system may oftentimes includes an external charger to recharge a neuromodulator, so that a surgical procedure to replace a power depleted neuromodulator can be avoided. To wirelessly convey energy between the external charger and the implanted neuromodulator, the charger typically includes an alternating current (AC) charging coil that supplies energy to a similar charging coil located in or on the neurostimulation device. The energy received by the charging coil located on the neuromodulator can then be used to directly power the electronic componentry contained within the neuromodulator, or can be stored in a rechargeable battery within the neuromodulator, which can then be used to power the electronic componentry on-demand.

In the context of an SCS procedure, one or more leads are introduced through the patient's back into the epidural space, such that the electrodes carried by the leads are arranged in a desired pattern and spacing to create an electrode array. After proper placement of the leads at the target area of the spinal cord, the leads are anchored in place at an exit site to prevent movement of the leads. To facilitate the location of the neuromodulator away from the exit point of the leads, lead extensions are sometimes used. The leads, or the lead extensions, are then connected to the IPG, which can then be operated to generate electrical pulses that are delivered, through the electrodes, to the targeted spinal cord tissue. The modulation, and in the conventional case, the stimulation, creates the sensation known as paresthesia, which can be characterized as an alternative sensation that replaces the pain signals sensed by the patient. The efficacy of SCS is related to the ability to modulate the spinal cord tissue corresponding to evoked paresthesia in the region of the body where the patient experiences pain. Thus, the working clinical paradigm is that achievement of an effective result from SCS depends on the neuromodulation lead or leads being placed in a location (both longitudinal and lateral) relative to the spinal tissue such that the electrical modulation will induce paresthesia located in approximately the same place in the patient's body as the pain (i.e., the target of treatment).

Conventional neuromodulation therapies employ electrical stimulation pulse trains at low- to mid-frequencies (e.g., less than 1500 Hz) to efficiently induce desired firing rate of action potentials from electrical pulses (e.g., one pulse can induce a burst of action potentials, or multiple pulses may be temporally integrated to induce on action potential). Such stimulation pulse trains are usually tonic (i.e., the pulse amplitude, pulse rate, and pulse width are fixed). However, neuron response is a dynamic time course that can vary with the sequential stimulation, thereby limiting the volume of neural tissue that may be consistently stimulated. Furthermore, it is known that neural tissue may accommodate, adapt, and/or habituate to a continuous tonic input, resulting in a diminished neural response over time.

Recently, high frequency modulation (e.g., 1.5 KHz-50 KHz), which has been increasingly attractive in neuromodulation for pain management, is employed to block naturally occurring action potentials within neural fibers or otherwise disrupt the action potentials within the neural fibers.

Although the underlying mechanisms of high frequency modulation for pain reduction are yet unclear, it has been hypothesized that there are many mechanisms that potentially play a role in reducing pain, including the depletion of neurotransmitter during the sustained modulation, desynchronized firing of multiple neurons, and generation of stochastic noise in neuronal signal transmission or lesioning of pain information. One disadvantage of high-frequency pulsed electrical energy is that it consumes an excessive amount of energy, thereby requiring the neuromodulator device to be charged more often.

Furthermore, although certain conventional stimulation parameters (e.g., pulse amplitude, pulse frequency, and pulse width) of the pulsed electrical energy, whether delivered at a low-, mid-, or high-frequency, can be varied to optimize the therapy, it may be desirable to allow the user to vary other characteristics of the pulsed electrical energy in order to further tailor the pulsed electrical energy to the volume of neural tissue to be modulated.

There, thus, remains an improved technique for delivering pulsed electrical energy to a patient.

SUMMARY OF THE INVENTION

In accordance with a first aspect of the present inventions, a neuromodulation system comprises a plurality of electrical terminals configured for being respectively coupled to a plurality of electrodes, a user interface configured for receiving input from a user that defines a shape of a modulating signal, and neuromodulation output circuitry configured for outputting an electrical pulse train to the plurality of electrical terminals. The neuromodulation system further comprises pulse train modulation circuitry configured for modulating the electrical pulse train in accordance with the defined shape of the modulating signal. In one embodiment, one of a pulse amplitude, a pulse rate, and a pulse duration of the electrical pulse train is modulated by the amplitude of the modulating signal. In another embodiment, the user input comprises a selection of one of a plurality of different predefined shapes of the modulating signal (e.g., at least two of a sinusoidal wave, a triangular wave, and a ramp wave). In still another embodiment, the user interface is configured for receiving another input from the user selecting an electrical pulse parameter of the electrical pulse train to be modulated, and the pulse train modulation circuitry is configured for modulating the selected electrical pulse parameter of the electrical pulse train in accordance with the defined shape of the modulating signal. The neuromodulation system may further comprise a casing containing the plurality of electrical terminals, the user interface, the neuromodulation output circuitry, and the electrical pulse modulation circuitry.

In accordance with a second aspect of the present inventions, a neuromodulation system comprises a plurality of electrical terminals configured for being respectively coupled to a plurality of electrodes, a user interface configured for receiving an input from a user selecting one of a plurality of different electrical pulse parameters for an electrical pulse train (e.g., at least two of a sinusoidal wave, a triangular wave, and a ramp wave), and neuromodulation output circuitry configured for outputting the electrical pulse train to the plurality of electrical terminals. The neuromodulation system further comprises pulse train modulation circuitry configured for modulating the selected electrical pulse parameter of the electrical pulse train. The neuromodulation system may further comprise a casing containing the plurality of electrical terminals, the user interface, the neuromodulation output circuitry, and the electrical pulse modulation circuitry.

In accordance with a third aspect of the present inventions, a neuromodulation system comprises a plurality of electrical terminals configured for being respectively coupled to a plurality of electrodes, neuromodulation output circuitry configured for outputting an electrical pulse train to the plurality of electrical terminals, and pulse train modulation circuitry configured for modulating a pulse rate of the electrical pulse train in accordance with a determinate modulating signal. The neuromodulation system may optionally comprise a user interface configured for receiving an input from a user defining a characteristic of the modulating signal. In one embodiment, the characteristic of the modulating signal is a shape of the modulating signal. In this case, the user input may comprise a selection of one of a plurality of different predefined shapes of the modulating signal (e.g., at least two of a sinusoidal wave, a triangular wave, and a ramp wave). The neuromodulation system may further comprise a casing containing the plurality of electrical terminals, the neuromodulation output circuitry, and the electrical pulse modulation circuitry.

In accordance with a fourth aspect of the present inventions, a neuromodulation system comprises a plurality of electrical terminals configured for being respectively coupled to a plurality of electrodes, neuromodulation output circuitry configured for outputting an electrical pulse train to the plurality of electrical terminals, and pulse train modulation circuitry configured for modulating a pulse duration of the electrical pulse train in accordance with a determinate modulating signal. The neuromodulation system may optionally comprise a user interface configured for receiving an input from a user defining a characteristic of the modulating signal. In one embodiment, the characteristic of the modulating signal is a shape of the modulating signal. In this case, the user input may comprise a selection of one of a plurality of different predefined shapes of the modulating signal (e.g., at least two of a sinusoidal wave, a triangular wave, and a ramp wave). The neuromodulation system may further comprise a casing containing the plurality of electrical terminals, the neuromodulation output circuitry, and the electrical pulse modulation circuitry.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 6c is a diagram illustrating a pulse amplitude of an electrical pulse train modulated with a ramped wave in accordance with one modulation technique performed by the SCM system of FIG. 1;

FIG. 6d is a diagram illustrating a pulse amplitude of an electrical pulse train modulated with a stepped sinusoidal wave in accordance with one modulation technique performed by the SCM system of FIG. 1;

FIG. 7c is a diagram illustrating a pulse rate of an electrical pulse train modulated with a ramped wave in accordance with one modulation technique performed by the SCM system of FIG. 1;

FIG. 8c is a diagram illustrating a pulse duration of an electrical pulse train modulated with a ramped wave in accordance with one modulation technique performed by the SCM system of FIG. 1;

DETAILED DESCRIPTION OF THE EMBODIMENTS

The description that follows relates to a spinal cord modulation (SCM) system. However, it is to be understood that while the invention lends itself well to applications in spinal cord modulation, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neurostimulator configured to treat urinary incontinence, sleep apnea, shoulder sublaxation, headache, etc.

Figure 1:
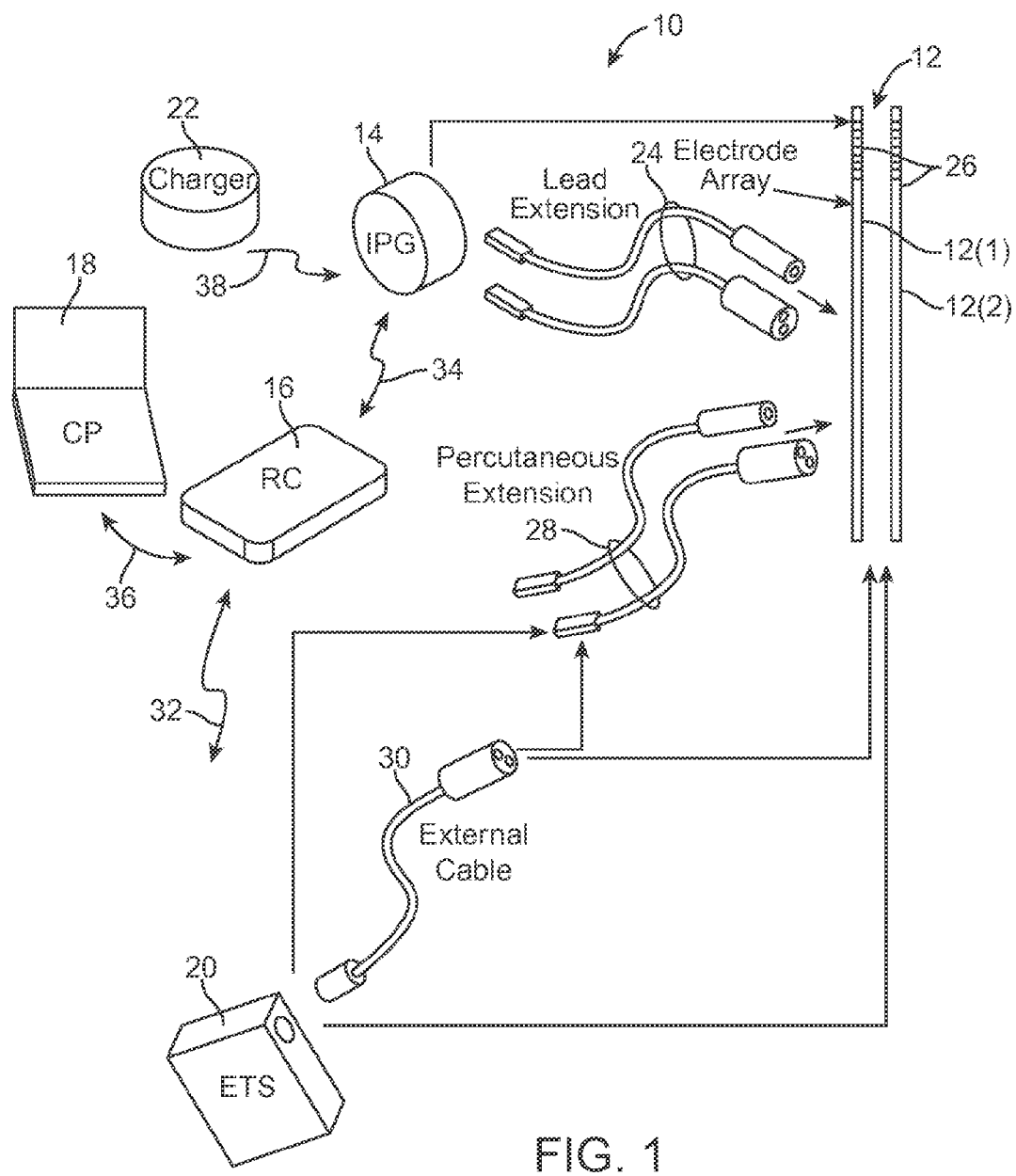
FIG. 1 is a plan view of an embodiment of a spinal cord modulation (SCM) system arranged in accordance with the present inventions.

Turning first to FIG. 1, an exemplary SCM neuromodulation system 10 generally includes one or more (in this case, two) implantable modulation leads 12, an implantable pulse generator (IPG) 14, an external remote controller RC 16, a clinician's programmer (CP) 18, an External Trial Modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 may be arranged in-line along the neuromodulation leads 12. In alternative embodiments, the electrodes 26 may be arranged in a two-dimensional pattern on a single paddle lead. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of neuromodulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of neuromodulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the stimulation that is to be provided. Thus, any functions described herein with respect to the IPG 14 can likewise be performed with respect to the ETM 20.

The RC 16 may be used to telemetrically control the ETM 20 via a bi-directional RF communications link 32. Once the IPG 14 and modulation leads 12 are implanted, the RC 16 may be used to telemetrically control the IPG 14 via a bi-directional RF communications link 34. Such control allows the IPG 14 to be turned on or off and to be programmed with different neuromodulation parameter sets. The IPG 14 may also be operated to modify the programmed neuromodulation parameters to actively control the characteristics of the electrical modulation energy output by the IPG 14. As will be described in further detail below, the CP 18 provides clinician detailed neuromodulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed neuromodulation parameters provided by the CP 18 are also used to program the RC 16, so that the neuromodulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Once the IPG 14 has been programmed, and its power source has been charged by the external charger 22 or otherwise replenished, the IPG 14 may function as programmed without the RC 16 or CP 18 being present.

For purposes of brevity, the details of the ETM 20 and external charger 22 will not be described herein. Details of exemplary embodiments of these devices are disclosed in U.S. Pat. No. 6,895,280, which is expressly incorporated herein by reference.

Figure 2:
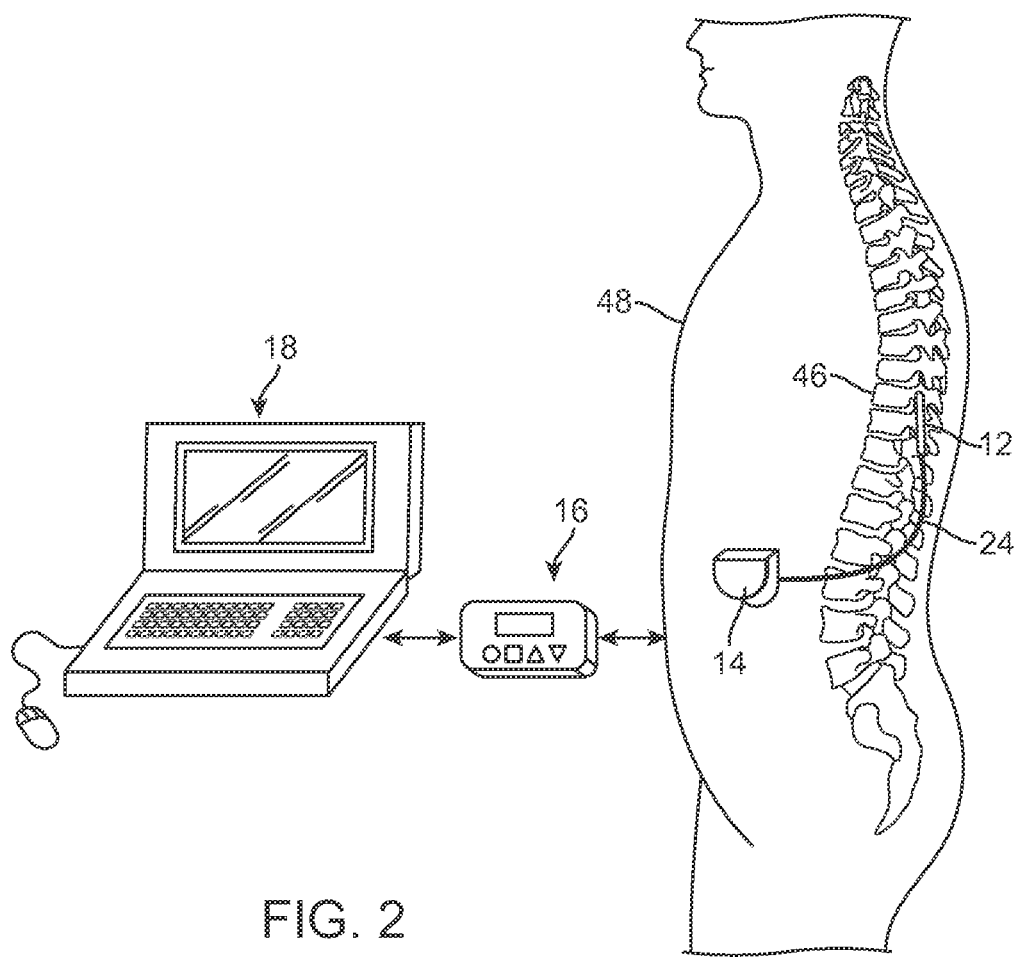
FIG. 2 is a plan view of the SCM system of FIG. 1 in use with a patient.

As shown in FIG. 2, the neuromodulation leads (or lead) 12 are implanted within the spinal column 42 of a patient 40. The preferred placement of the neuromodulation leads 12 is adjacent, i.e., resting near, or upon the dura, adjacent to the spinal cord area to be stimulated. The neuromodulation leads 12 will be located in a vertebral position that depends upon the location and distribution of the chronic pain. For example, if the chronic pain is in the lower back or legs, the neuromodulation leads 12 may be located in the mid- to low-thoracic region (e.g., at the T9-12 vertebral levels). Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
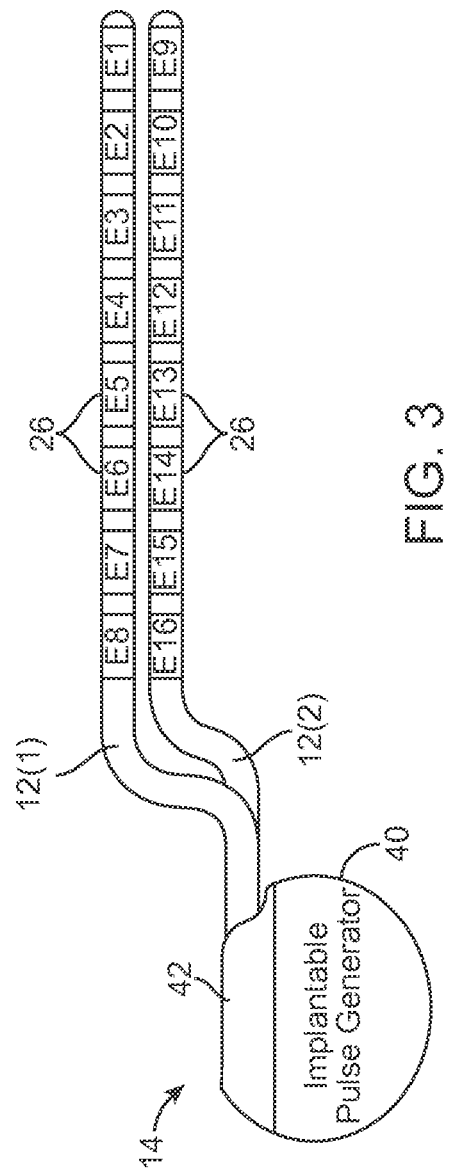
FIG. 3 is a profile view of an implantable pulse generator (IPG) and percutaneous leads used in the SCM system of FIG. 1.

Referring now to FIG. 3, the features of the neuromodulation leads 12 and the IPG 14 will be briefly described. One of the neuromodulation leads 12(1) has eight electrodes 26 (labeled E1-E8), and the other modulation lead 12(2) has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neuromodulation leads 12 mates in a manner that electrically couples the electrodes 26 to the electronics within the outer case 40. The outer case 44 is composed of an electrically conductive, biocompatible material, such as titanium, and forms a hermetically sealed compartment wherein the internal electronics are protected from the body tissue and fluids. In some cases, the outer case 40 may serve as an electrode.

As will be described in further detail below, the IPG 14 includes a battery and pulse generation circuitry that delivers the electrical modulation energy in the form of one or more electrical pulse trains to the electrode array 26 in accordance with a set of neuromodulation parameters programmed into the IPG 14. Such neuromodulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the modulation on duration X and modulation off duration Y).

Figure 4:
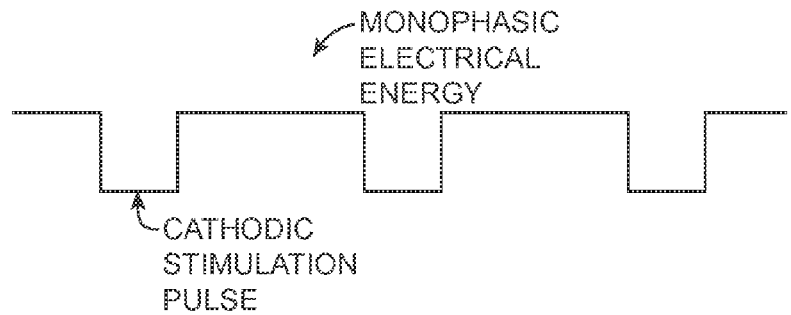
FIG. 4 is a plot of monophasic cathodic electrical modulation energy.

Electrical modulation will occur between two (or more) activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case of the IPG 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12(1) may be activated as an anode at the same time that electrode E11 on the second lead 12(1) is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode The modulation energy may be delivered between a specified group of electrodes as monophasic electrical energy or multiphasic electrical energy. As illustrated in FIG. 4, monophasic electrical energy takes the form of an electrical pulse train that includes either all negative pulses (cathodic), or alternatively all positive pulses (anodic).

Figure 5A:
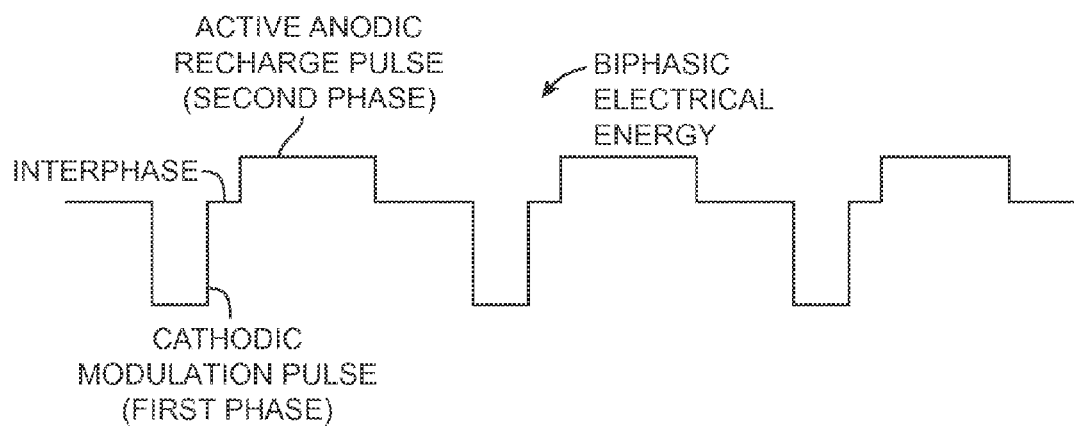
FIG. 5a is a plot of biphasic electrical modulation energy having a cathodic modulation pulse and an active charge recovery pulse.
Figure 5B:
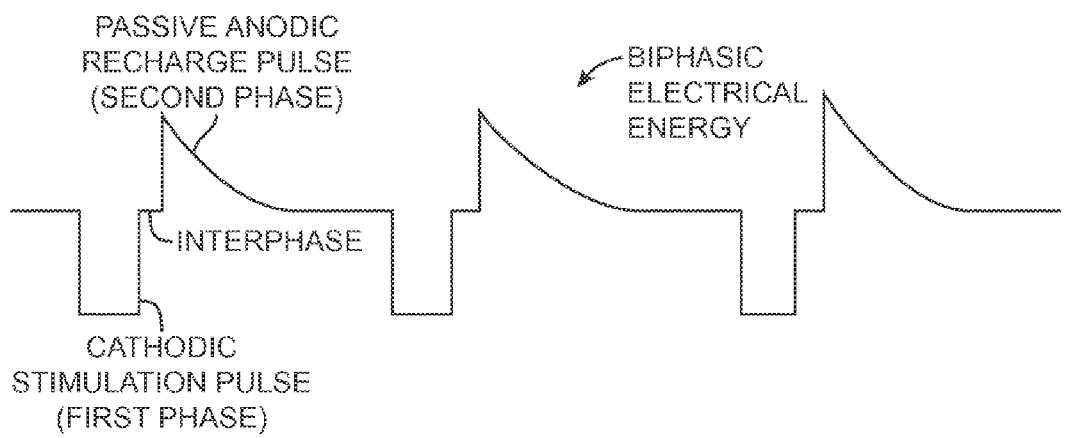
FIG. 5b is a plot of biphasic electrical modulation energy having a cathodic modulation pulse and a passive charge recovery pulse.

Multiphasic electrical energy includes a series of pulses that alternate between positive and negative. For example, as illustrated in FIGS. 5a and 5b, multiphasic electrical energy may include a series of biphasic pulses, with each biphasic pulse including a cathodic (negative) modulation pulse (during a first phase) and an anodic (positive) charge recovery pulse (during a second phase) that is generated after the modulation pulse to prevent direct current charge transfer through the tissue, thereby avoiding electrode degradation and cell trauma. That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the charge recovery pulse).

The second phase may have an active charge recovery pulse (FIG. 5a), wherein electrical current is actively conveyed through the electrode via current or voltage sources, and a passive charge recovery pulse, or the second phase may have a passive charge recovery pulse (FIG. 5b), wherein electrical current is passively conveyed through the electrode via redistribution of the charge flowing from coupling capacitances present in the circuit. Using active recharge, as opposed to passive recharge, allows faster recharge, while avoiding the charge imbalance that could otherwise occur. Another electrical pulse parameter in the form of an interphase can define the time period between the pulses of the biphasic pulse (measured in microseconds).

Significant to the present inventions, the SCM system 10 is capable of allowing a user to define an electrical pulse parameter (e.g., a pulse amplitude, pulse rate, and/or a pulse duration) of an electrical pulse train that is to be modulated with a determinate modulation signal. The SCM system may also be capable of allowing a user to define the shape (e.g., sinusoidal, triangular, ramp, etc) of the modulation signal that is to be used to modulate the electrical pulse train. In this manner, more flexibility is provided to the user to tailor the pulsed electrical energy to the targeted volume of neural tissue to be modulated. Furthermore, for low- or mid-frequency applications (i.e., less than 1500 Hz), accommodation of the neural tissue may be prevented or otherwise minimized without having to expend a considerable amount of energy that might otherwise occur by utilizing high-frequency electrical energy. It is also proposed that the modulation of a low- or mid-frequency pulse train may desynchronize the firing of action potentials in the neural tissue at a reduced energy consumption.

Figure 6A:
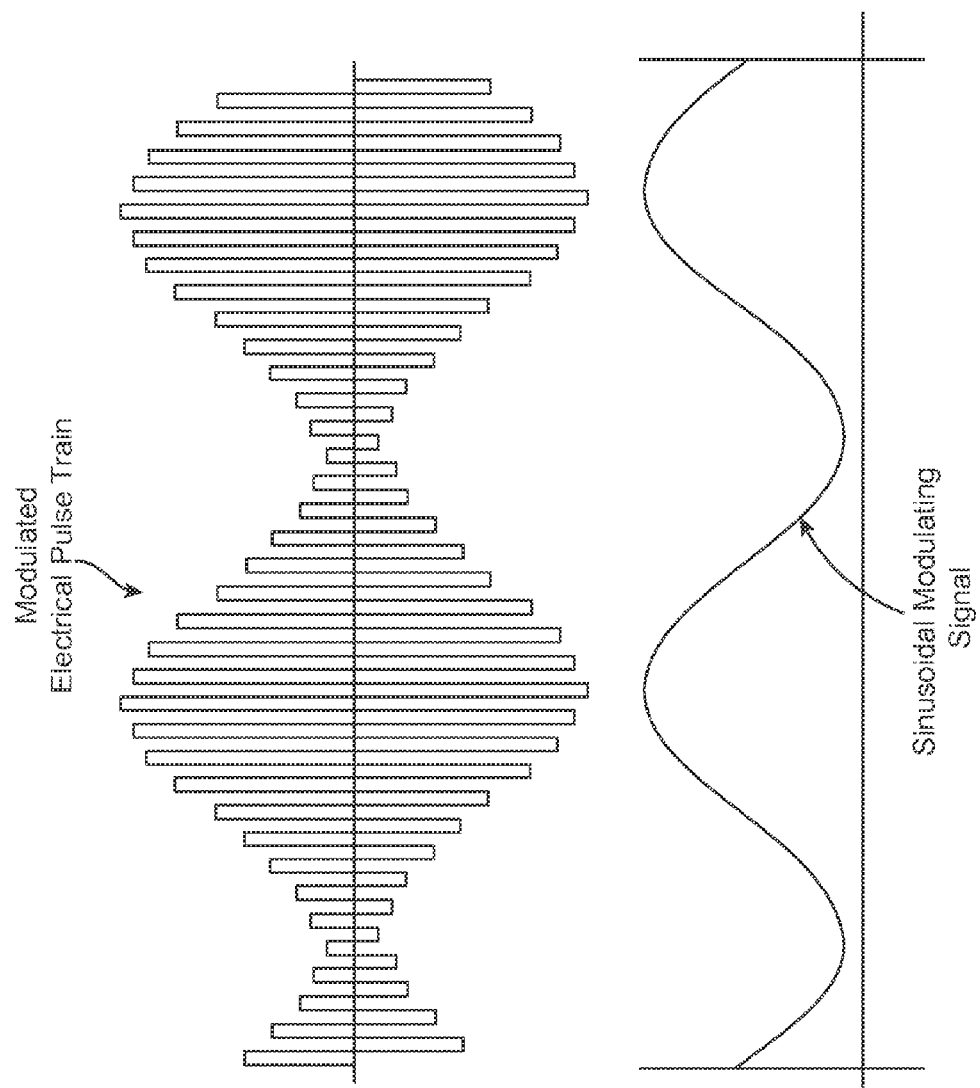
FIG. 6a is a diagram illustrating a pulse amplitude of an electrical pulse train modulated with a sinusoidal wave in accordance with one modulation technique performed by the SCM system of FIG. 1.
Figure 6B:
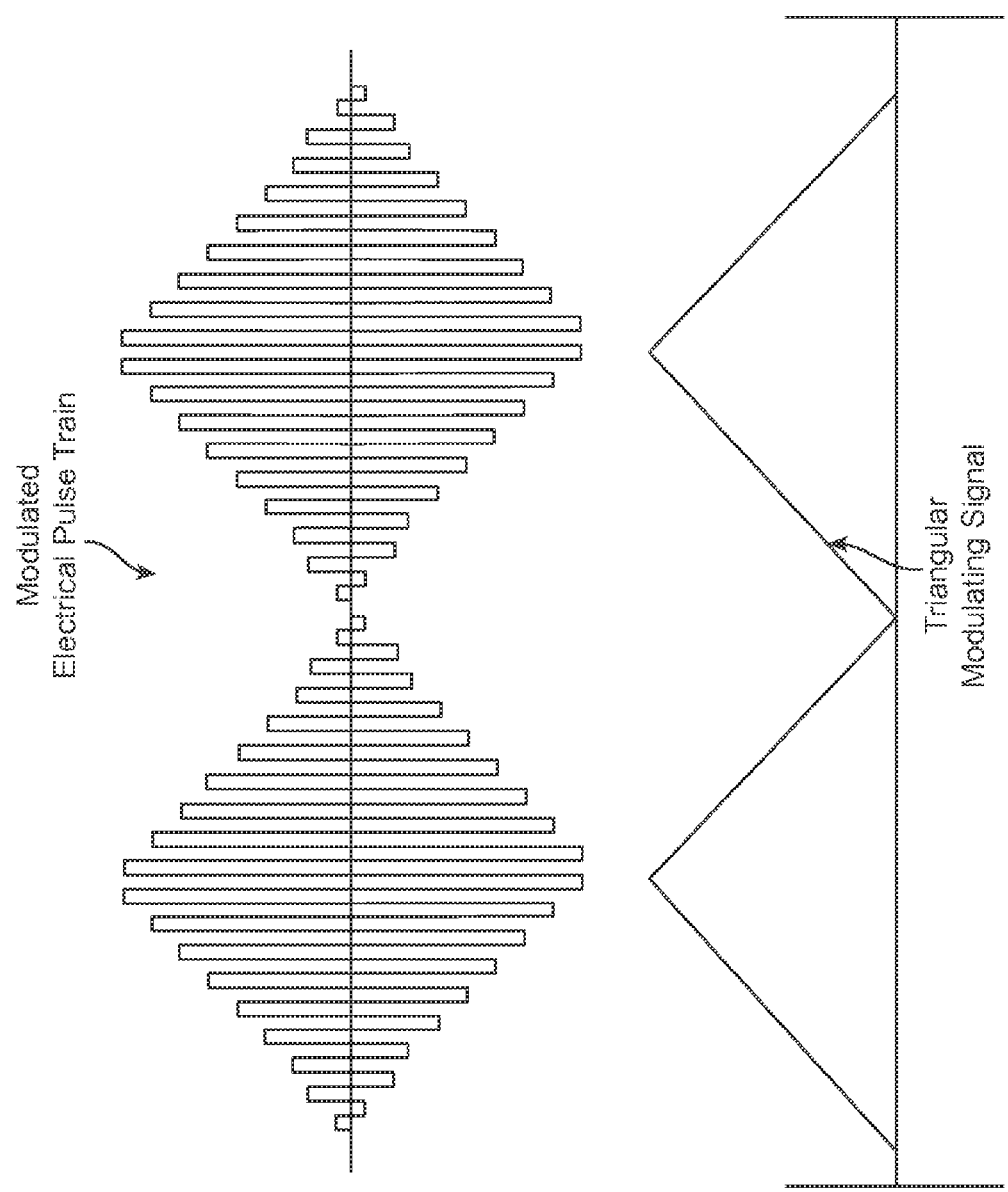
FIG. 6b is a diagram illustrating a pulse amplitude of an electrical pulse train modulated with a triangular wave in accordance with one modulation technique performed by the SCM system of FIG. 1.

The amplitude of a relatively high frequency electrical pulse train may be modulated by a relatively low frequency modulating signal to create an electrical pulse train having an envelope that varies in accordance with the amplitude of the modulating signal (i.e., as the amplitude of the modulating signal increases, the envelope of electrical pulse train increases, and as the amplitude of the modulating signal decreases, the envelope of the electrical pulse train decreases). For example, as illustrated in FIG. 6a, the amplitude of an electrical pulse train can be modulated by a sinusoidal modulating signal to create an electrical pulse train with a sinusoid shaped envelope. As illustrated in FIG. 6b, the amplitude of an electrical pulse train can be modulated by a triangular modulating signal to create an electrical pulse train with a triangle shaped envelope. As illustrated in FIG. 6c, the amplitude of an electrical pulse train can be modulated by a ramped modulating signal to create an electrical pulse train with a ramp shaped envelope. Although the ramped modulating signal is shown as being linearly increasing, the ramped modulating signal may alternatively be linearly decreasing, or even non-linearly increasing or decreasing (e.g., exponential). The electrical pulse train can be alternately turned on and off to create a modulated bursted electrical pulse train. For example, as illustrated in FIG. 6d, the amplitude of an electrical pulse train can be modulated by the combination of a sinusoidal modulating signal and a stepped signal to create a bursted electrical pulse train with a sinusoid shaped envelope.

Figure 7A:
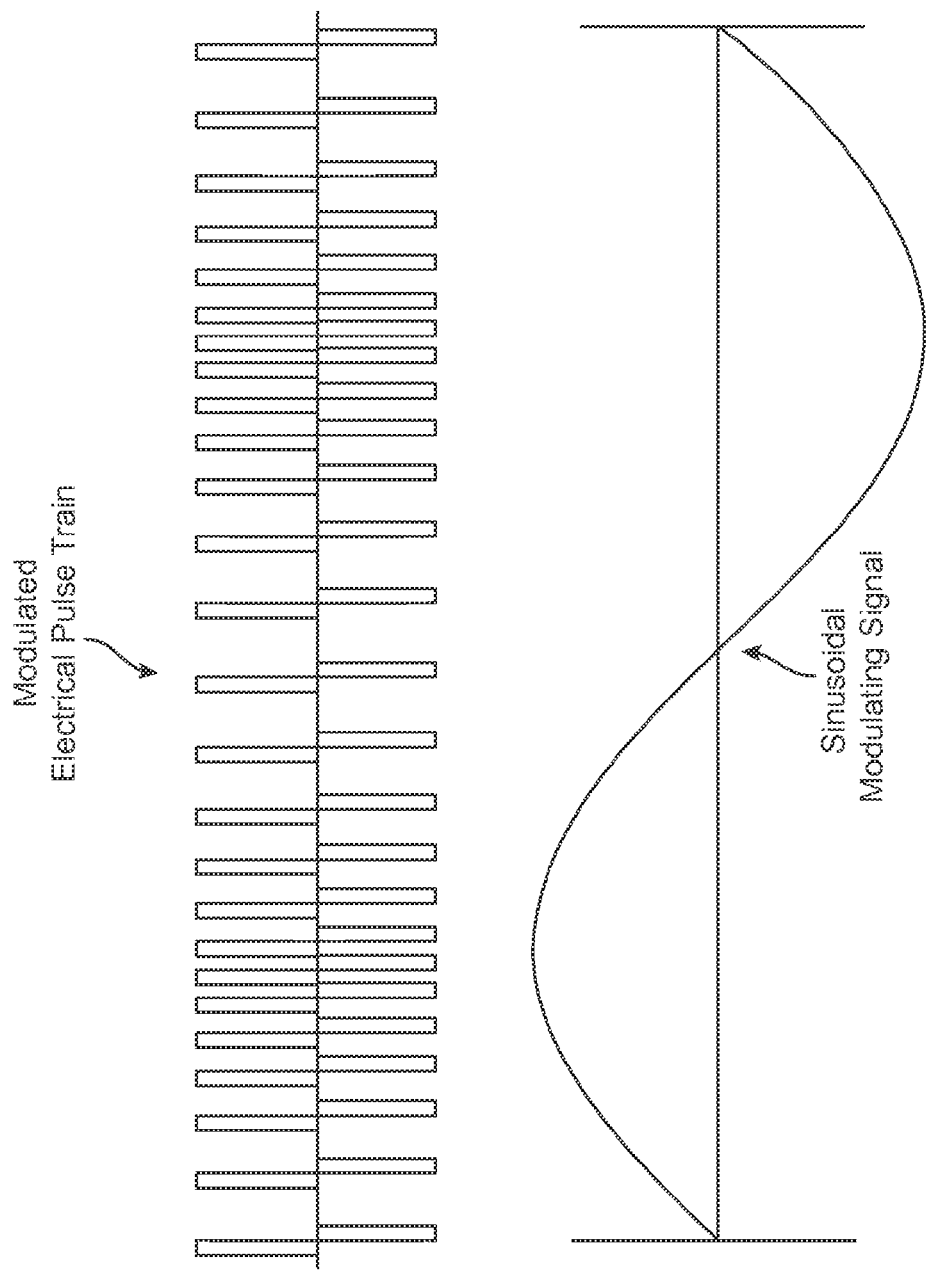
FIG. 7a is a diagram illustrating a pulse rate of an electrical pulse train modulated with a sinusoidal wave in accordance with one modulation technique performed by the SCM system of FIG. 1.
Figure 7B:
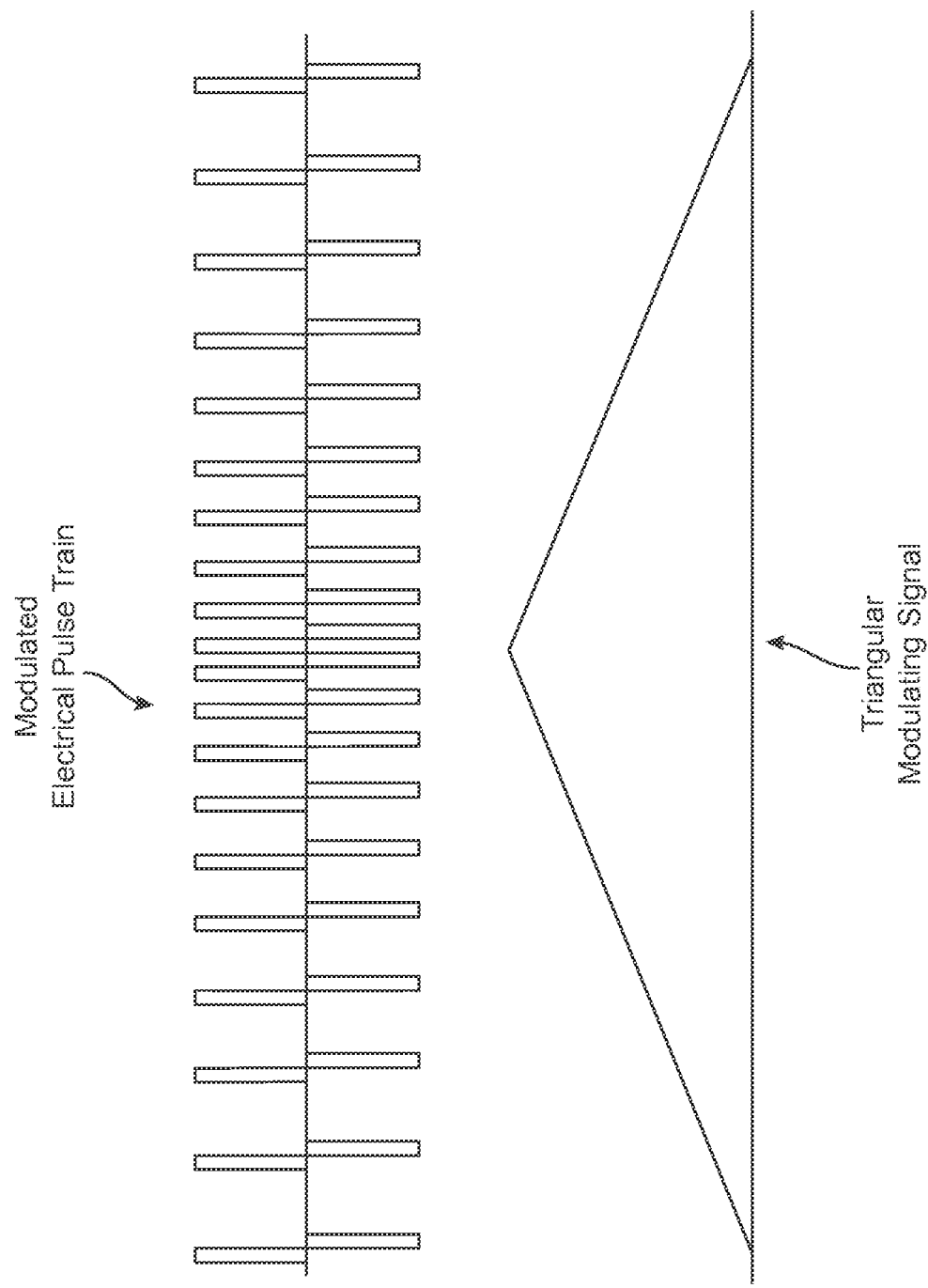
FIG. 7b is a diagram illustrating a pulse rate of an electrical pulse train modulated with a triangular wave in accordance with one modulation technique performed by the SCM system of FIG. 1.

The pulse rate of a relatively high frequency electrical pulse train may be modulated by a relatively low frequency modulating signal to create an electrical pulse train having a pulse rate that varies in accordance with the amplitude of the modulating signal (i.e., as the amplitude of the modulating signal increases, the pulse rate increases, and as the amplitude of the modulating signal decreases, the pulse rate decreases). For example, as illustrated in FIG. 7a, the pulse rate of an electrical pulse train can be modulated by a sinusoidal modulating signal to create an electrical pulse train having a pulse rate that varies in accordance with the amplitude of the sinusoidal modulating signal. As illustrated in FIG. 7b, the pulse rate of an electrical pulse train can be modulated by a triangular modulating signal to create an electrical pulse train having a pulse rate that varies in accordance with the amplitude of the triangular modulating signal. As illustrated in FIG. 7c, the pulse rate of an electrical pulse train can be modulated by a ramped modulating signal to create an electrical pulse train having a pulse rate that varies in accordance with the amplitude of the ramped modulating signal. Although a single timing channel is utilized to create the modulated electrical pulse trains illustrated in FIGS. 7a-7c, electrical pulse trains with different pulse rates can be bursted on and off in multiple timing channels to create a single electrical pulse train with a modulated pulse rate, as described in U.S. Provisional Patent Application Ser. No. 61/768,286, entitled "Multi-Channel Neuromodulation System Having Frequency Modulated Stimulation," which is expressly incorporated herein by reference.

Figure 8A:
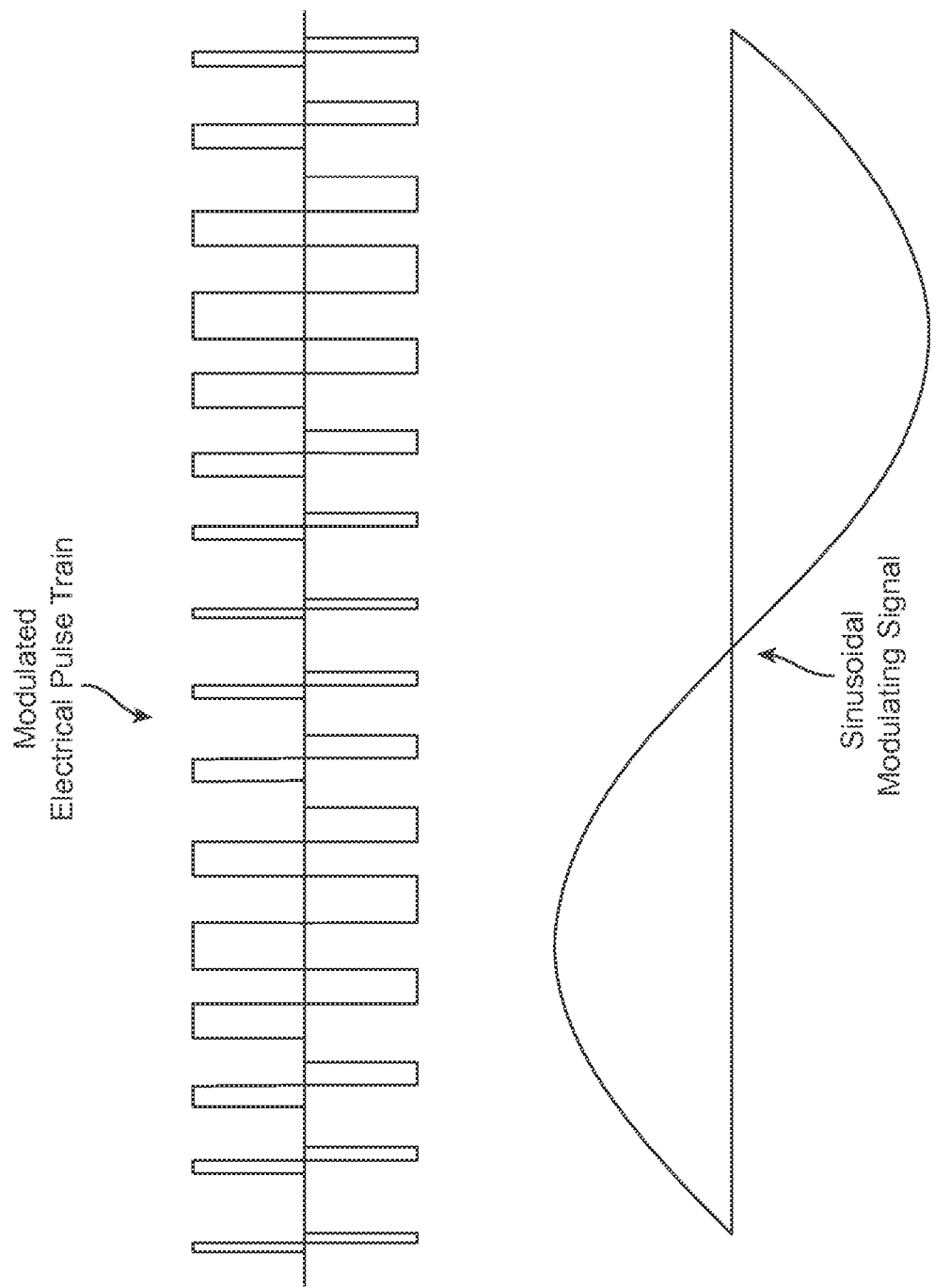
FIG. 8a is a diagram illustrating a pulse duration of an electrical pulse train modulated with a sinusoidal wave in accordance with one modulation technique performed by the SCM system of FIG. 1.
Figure 8B:
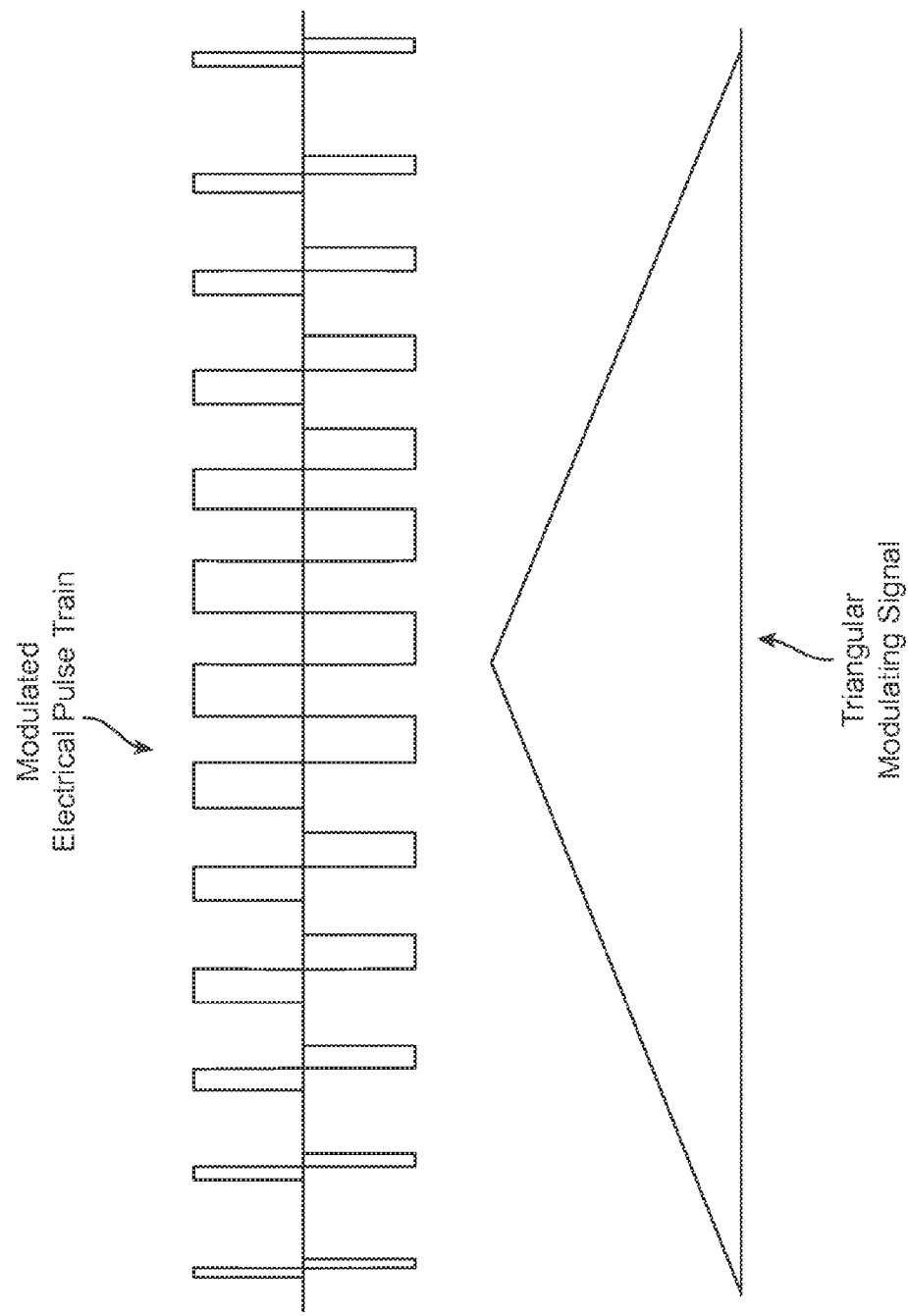
FIG. 8b is a diagram illustrating a pulse duration of an electrical pulse train modulated with a triangular wave in accordance with one modulation technique performed by the SCM system of FIG. 1.

The pulse duration of a relatively high frequency electrical pulse train may be modulated by a relatively low frequency modulating signal to create an electrical pulse train having a pulse duration that varies in accordance with the amplitude of the modulating signal (i.e., as the amplitude of the modulating signal increases, the pulse duration increases, and as the amplitude of the modulating signal decreases, the pulse duration decreases). For example, as illustrated in FIG. 8a, the pulse duration of an electrical pulse train can be modulated by a sinusoidal modulating signal to create an electrical pulse train having a pulse duration that varies in accordance with the amplitude of the sinusoidal modulating signal. As illustrated in FIG. 8b, the pulse duration of an electrical pulse train can be modulated by a triangular modulating signal to create an electrical pulse train having a pulse duration that varies in accordance with the amplitude of the triangular modulating signal. As illustrated in FIG. 8c, the pulse duration of an electrical pulse train can be modulated by a ramped modulating signal to create an electrical pulse train having a pulse duration that varies in accordance with the amplitude of the ramped modulating signal.

Although the modulations of the electrical pulse trains illustrated above are biphasic in nature, it should be appreciated that the modulation of an electrical pulse train can be monophasic in nature; for example, by modulating the amplitudes of only the cathodic phases of the electrical pulse train.

Figure 9:
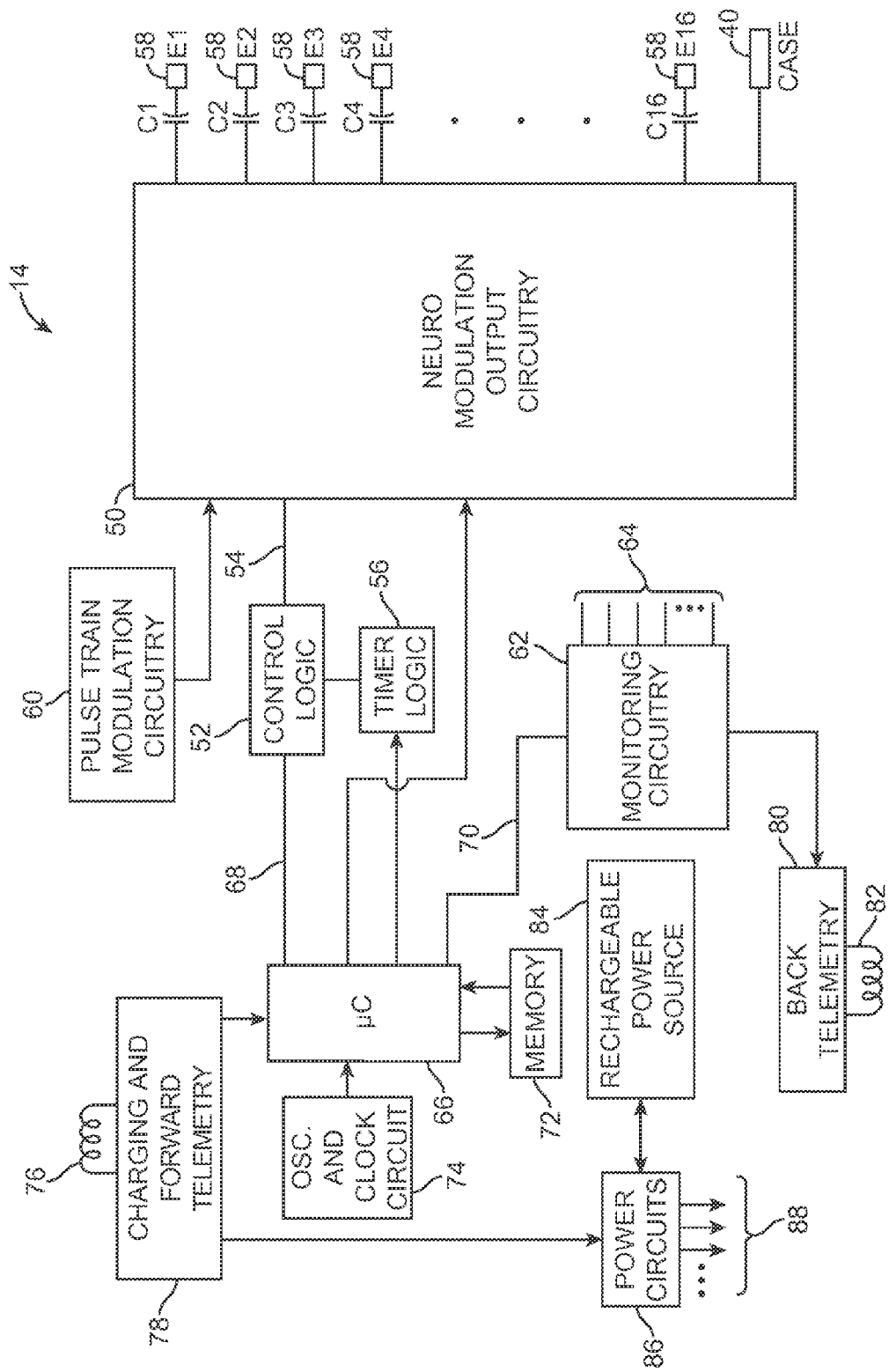
FIG. 9 is a block diagram of the internal components of the IPG of FIG. 3.

Turning next to FIG. 9, the main internal components of the IPG 14 will now be described. The IPG 14 includes neuromodulation output circuitry 50 configured for generating electrical modulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 µs. The neuromodulation energy generated by the neuromodulation output circuitry 50 is output via capacitors C1-C16 to electrical terminals 58 corresponding to the electrodes 26. The neuromodulation circuitry 50 may either comprise independently controlled current sources for providing modulation pulses of a specified and known amperage to or from the electrodes 26, or independently controlled voltage sources for providing modulation pulses of a specified and known voltage at the electrodes 26.

Any of the N electrodes may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary, e.g., as controlled by the RC 16. External programming software in the CP 18 is typically used to set neuromodulation parameters including electrode polarity, amplitude, pulse rate and pulse duration for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a multipolar (e.g., bipolar) mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode may be programmed to one of several discrete current levels, e.g., between 0 to 10 mA in steps of 0.1 mA. Also, the pulse duration of the current pulses is preferably adjustable in convenient increments, e.g., from 0 to 1 milliseconds (ms) in increments of 10 microseconds (μs). Similarly, the pulse rate is preferably adjustable within acceptable limits, e.g., from 0 to 50000 pulses per second (pps). Other programmable features can include slow start/end ramping, burst modulation cycling (on for X time, off for Y time), interphase, and open or closed loop sensing modes.

The operation of this neuromodulation output circuitry 50, including alternative embodiments of suitable output circuitry for performing the same function of generating modulation pulses of a prescribed amplitude and duration, is described more fully in U.S. Pat. Nos. 6,516,227 and 6,993, 384, which are expressly incorporated herein by reference.

The IPG 14 further comprises pulse train modulation circuitry 60 configured for using predeterminate modulation signals (e.g., the modulating signals illustrated in FIGS. 6-8 to modulate electrical pulse train output by the neuromodulation output circuitry 50 to the electrical terminals 58. In response to user input, as will be described in further detail below, the modulation circuitry 60 may advantageously select the particular electrical parameter (e.g., pulse amplitude, pulse rate, and/or pulse duration) of the electrical pulse train and/or select the shape of the modulation signal (e.g., sinusoidal, triangular, ramped, etc.) used to modulate the electrical pulse train. The modulation circuitry 60 may be analog-based and incorporated into the output of the neuromodulation output circuitry 50 and/or may be digitally-based and incorporated into the control logic 52 and timer logic circuitry 56.

The IPG 14 further comprises monitoring circuitry 62 for monitoring the status of various nodes or other points 64 throughout the IPG 14, e.g., power supply voltages, temperature, battery voltage, and the like. The IPG 14 further comprises processing circuitry in the form of a microcontroller (μC) 66 that controls the control logic over data bus 68, and obtains status data from the monitoring circuitry 62 via data bus 70. The IPG 14 additionally controls the timer logic 56. The IPG 14 further comprises memory 72 and oscillator and clock circuitry 74 coupled to the microcontroller 66. The microcontroller 66, in combination with the memory 72 and oscillator and clock circuitry 74, thus comprise a microprocessor system that carries out a program function in accordance with a suitable program stored in the memory 72. Alternatively, for some applications, the function provided by the microprocessor system may be carried out by a suitable state machine.

Thus, the microcontroller 66 generates the necessary control and status signals, which allow the microcontroller 66 to control the operation of the IPG 14 in accordance with a selected operating program and neuromodulation parameters stored in the memory 72. In controlling the operation of the IPG 14, the microcontroller 66 is able to individually generate an electrical pulse train at the electrodes 26 using the neuromodulation output circuitry 50, in combination with the control logic 52 and timer logic 56, thereby allowing each electrode 26 to be paired or grouped with other electrodes 26, including the monopolar case electrode. In accordance with neuromodulation parameters stored within the memory 72, the microcontroller 66 may control the polarity, amplitude, rate, pulse duration and timing channel through which the modulation pulses are provided.

Thus, it can be appreciated that, under control of the microcontroller 66, the neuromodulation output circuitry 50 is configured for outputting a k number of individual electrical pulse trains respectively in a k number of timing channels to the electrical terminals 58. In the IPG 14, up to four stimulation programs may be stored in the memory 72, with each stimulation program having four timing channels. Thus, each modulation program defines four sets of neuromodulation parameters for four respective timing channels. Of course, the IPG 14 may have less or more than four modulation programs, and less or more than four timing channels for each modulation program. Significantly, the microcontroller 66 controls the modulation circuitry 60 in a manner that, for each timing channel, modulates the electrical pulse train in accordance with the electrical pulse parameter and/or shape of the modulating signal selected by the user.

The IPG 14 further comprises an alternating current (AC) receiving coil 76 for receiving programming data (e.g., the operating program, neuromodulation parameters, electrical parameters to be modulated, and/or the shape of the modulating signal) from the RC 16 (shown in FIG. 2) in an appropriate modulated carrier signal, and charging and forward telemetry circuitry 78 for demodulating the carrier signal it receives through the AC receiving coil 76 to recover the programming data, which programming data is then stored within the memory 72, or within other memory elements (not shown) distributed throughout the IPG 14.

The IPG 14 further comprises back telemetry circuitry 60 and an alternating current (AC) transmission coil 82 for sending informational data sensed through the monitoring circuitry 62 to the RC 16. The back telemetry features of the IPG 14 also allow its status to be checked. For example, when the RC 16 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16, all programmable settings stored within the IPG 14 may be uploaded to the RC 16. Significantly, the back telemetry features allow raw or processed electrical parameter data (or other parameter data) previously stored in the memory 72 to be downloaded from the IPG 14 to the RC 16, which information can be used to track the physical activity of the patient.

The IPG 14 further comprises a rechargeable power source 84 and power circuits 86 for providing the operating power to the IPG 14. The rechargeable power source 84 may, e.g., comprise a lithium-ion or lithium-ion polymer battery. The rechargeable battery 84 provides an unregulated voltage to the power circuits 86. The power circuits 86, in turn, generate the various voltages 88, some of which are regulated and some of which are not, as needed by the various circuits located within the IPG 14. The rechargeable power source 84 is recharged using rectified AC power (or DC power converted from AC power through other means, e.g., efficient AC-to-DC converter circuits, also known as "inverter circuits") received by the AC receiving coil 76. To recharge the power source 84, an external charger (not shown), which generates the AC magnetic field, is placed against, or otherwise adjacent, to the patient's skin over the implanted IPG 14. The AC magnetic field emitted by the external charger induces AC currents in the AC receiving coil 76. The charging and forward telemetry circuitry 78 rectifies the AC current to produce DC current, which is used to charge the power source 84. While the AC receiving coil 76 is described as being used for both wirelessly receiving communications (e.g., programming and control data) and charging energy from the external device, it should be appreciated that the AC receiving coil 76 can be arranged as a dedicated charging coil, while another coil, such as coil 82, can be used for bi-directional telemetry.

It should be noted that the diagram of FIG. 9 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCM system 10 may alternatively utilize an implantable receiver-stimulator (not shown) connected to the neuromodulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the modulation in accordance with the control signals.

Figure 10:
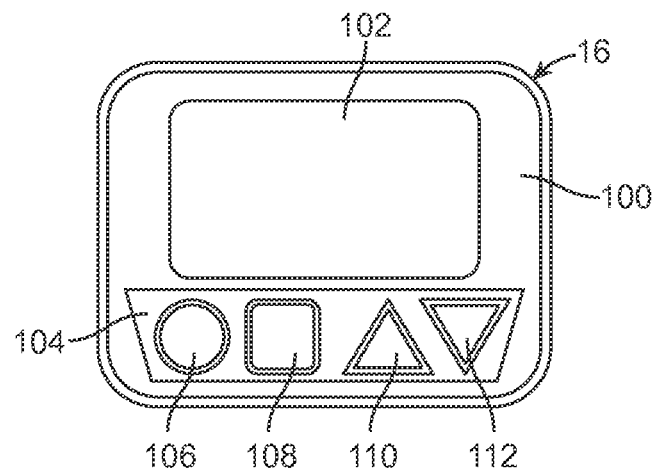
FIG. 10 is front view of a remote control (RC) used in the neuromodulation system of FIG. 1.
Figure 11:
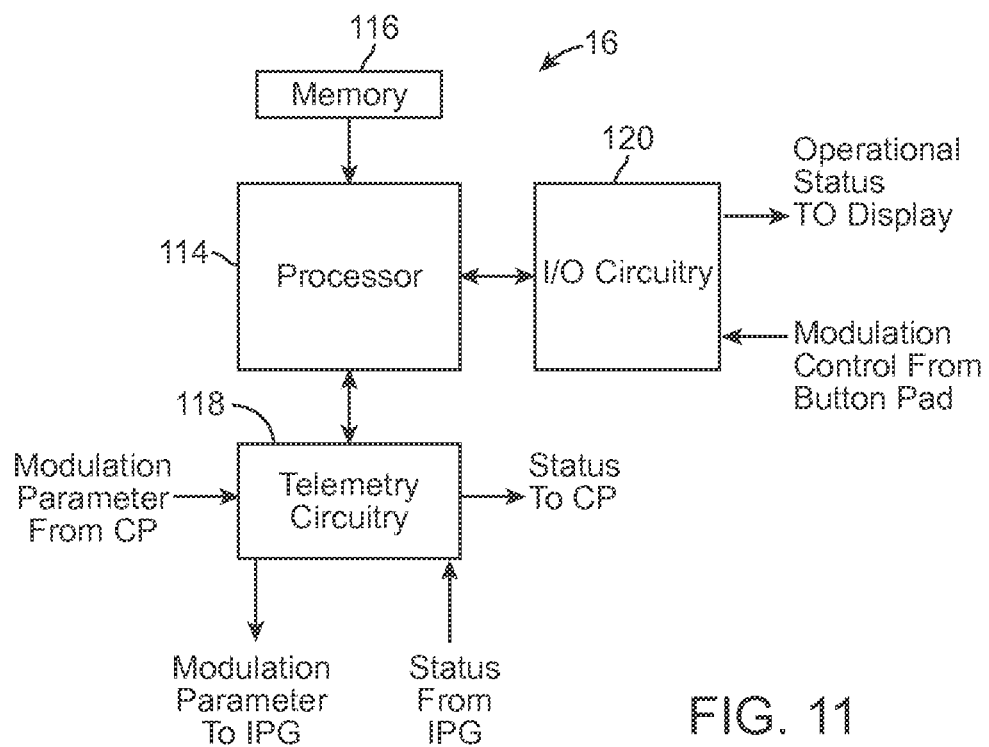
FIG. 11 is a block diagram of the internal components of the RC of FIG. 10.

Referring now to FIG. 10, one exemplary embodiment of an RC 16 is described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 includes a membrane switch with metal domes positioned over a flex circuit, and a keypad connector connected directly to a PCB. In an optional embodiment, the display screen 102 has touch-screen capabilities. The button pad 104 includes a multitude of buttons 106, 108, 110, and 112, which allow the IPG 14 to be turned ON and OFF, provide for the adjustment or setting of neuromodulation parameters within the IPG 14, and provide for selection between screens. The button pad 104 also allows the user to select the electrical pulse parameters to be modulated and/or the shape of the modulating signal used to modulate the electrical pulse train, as will be described in further detail below.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can be actuated to increase or decrease any of stimulation parameters of the pulse generated by the IPG 14, including the pulse amplitude, pulse width, and pulse rate. For example, the selection button 108 can be actuated to place the RC 16 in a "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112. Alternatively, dedicated up/down buttons can be provided for each stimulation parameter. Rather than using up/down buttons, any other type of actuator, such as a dial, slider bar, keypad, or touch screen can be used to increment or decrement the stimulation parameters.

Figure 12:
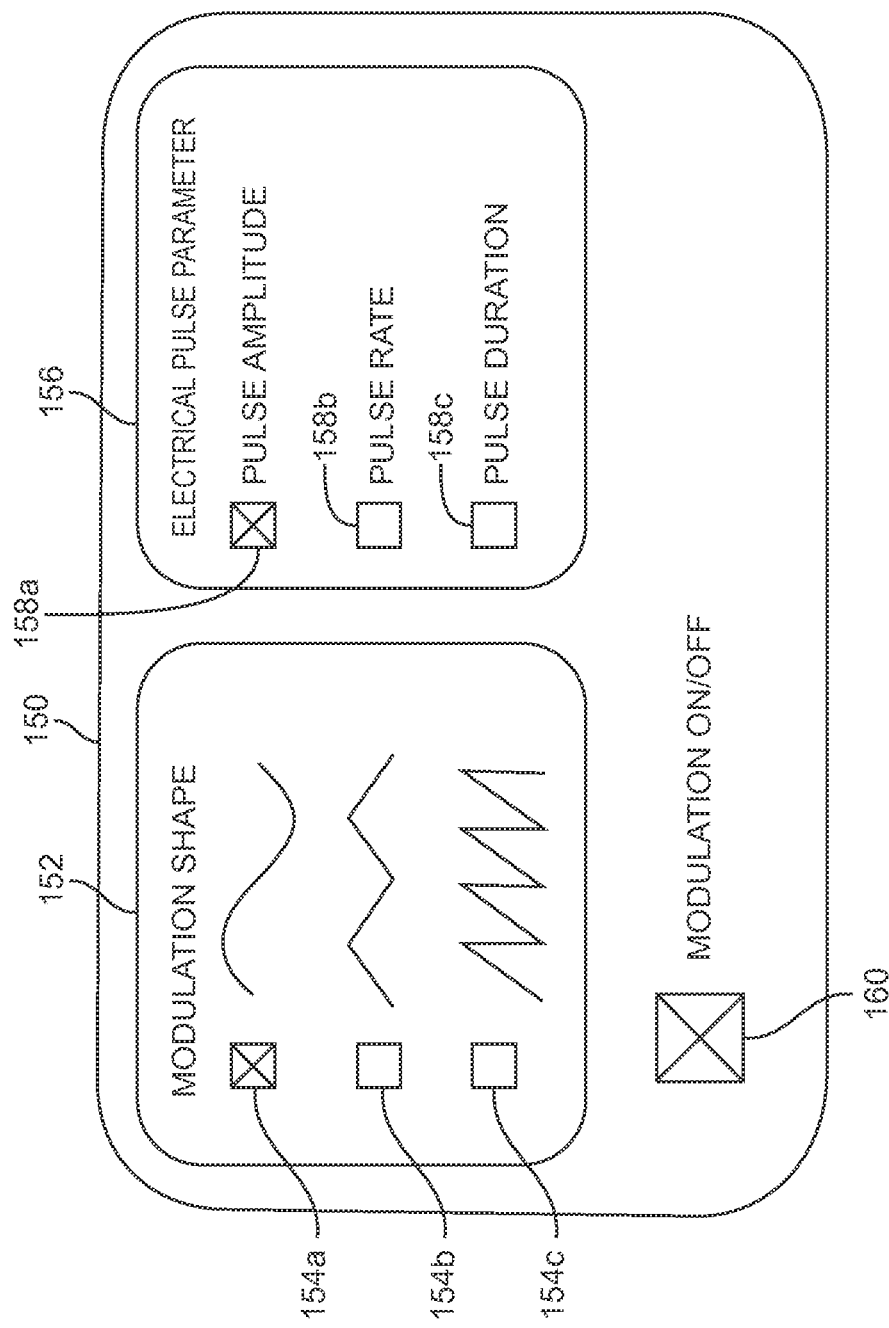
FIG. 12 is a plan view of a programming screen generated by the RC of FIG. 10 for modulating an electrical pulse train.

The selection button 108 can also be actuated to place the RC 16 in an "pulse train modulation mode" that allows a user modulate the electrical pulse train output by the IPG 14 in one of the timing channels and to select the electrical pulse parameter to be modulated and/or the shape of the modulating signal. For example, referring to FIG. 12, a programming screen 150 includes a modulation shape box 152 that includes a sinusoidal wave 154a, a triangular wave 154b, and a ramped wave 154c, and corresponding check boxes, any of which can be selected by the user using the button pad 104 to select the shape of the modulating signal used to modulate the electrical pulse train. Optionally, the programming screen 150 has a modulating parameter control (not shown) that allows the user to specify modulation parameters (e.g., upper and lower limit of the modulation shape, period of modulating signal, such as the sinusoidal wave, slope of a ramped wave, etc. The programming screen 150 also includes a modulated electrical pulse parameter box 156 that includes a pulse amplitude check box 158a, a pulse rate check box 158b, and a pulse duration check box 158c, any combination of which can be checked using the button pad 104 to allow the user to select the electrical pulse parameters of the electrical pulse train to be modulated. The programming screen 150 also includes an ON/OFF check box 160 that can be checked to turn the modulation feature on and unchecked to turn the modulation feature off. When the feature is turned on, the IPG 14 will modulate the selected electrical pulse parameter or parameters of the electrical pulse train using the modulating signal with the selected shape. The buttons 110 and 112 serve as up/down buttons that can be actuated to increase or decrease the amplitude of the modulating signal.

Although the foregoing programming functions have been described as being at least partially implemented in the RC 16, it should be noted that these techniques may be at least, in part, be alternatively or additionally implemented in the CP 18. Those skilled in the art will be able to fashion appropriate circuitry, whether embodied in digital circuits, analog circuits, software and/or firmware, or combinations thereof, in order to accomplish the desired functions.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neuromodulation system for modulating neural tissue by delivering a modulated electrical pulse train to the neural tissue, the neuromodulation system comprising:
neuromodulation output circuitry configured to output an electrical pulse train;

pulse train modulation circuitry configured to modulate the electrical pulse train output by the neuromodulation output circuitry with a modulation signal that has a defined shape selected from a group of preprogrammed shapes to provide the modulated electrical pulse train to modulate the neural tissue; and a user interface configured to receive a shape selection from the user, wherein the shape selection is a selected one of the group of preprogrammed shapes for use as the defined shape of the modulation signal.

2. The neuromodulation system of claim 1, wherein the electrical pulse train has an amplitude, and the pulse train modulation circuitry is configured to modulate the amplitude of the electrical pulse train with the defined shape of the modulation parameter.

3. The neuromodulation system of claim 1, wherein the electrical pulse train has a pulse rate, and the pulse train modulation circuitry is configured to modulate the pulse rate of the electrical pulse train with the defined shape of the modulation parameter.

4. The neuromodulation system of claim 1, wherein the electrical pulse train has an amplitude, a pulse duration, and the pulse train modulation circuitry is configured to modulate the pulse duration of the electrical pulse train with the defined shape of the modulation parameter.

5. The neuromodulation system of claim 1, wherein the electrical pulse train has an amplitude, a pulse rate and a pulse duration, and the pulse train modulation circuitry is configured to modulate more than one of the amplitude, the pulse rate and the pulse duration of the electrical pulse train with the defined shape of the modulation parameter.

6. The neuromodulation system of claim 1, wherein the group of preprogrammed shapes include at least two of a sinusoidal wave, a triangular wave, and a ramp wave.

7. The neuromodulation system of claim 1, wherein:
the electrical pulse train has a plurality of parameters;
the user input is configured to receive at least one parameter selection from the user wherein the at least one parameter is selected from the plurality of parameters, the at least one parameter selection to define at least one parameter of the electrical pulse train to be modulated with the modulation signal that has the defined shape.

8. The neuromodulation system of claim 1, wherein the system is a spinal cord modulation system.

9. The neuromodulation system of claim 1, wherein the system is a deep brain stimulation system.

10. The neuromodulation system of claim 1, wherein the pulse train modulation circuitry is analog modulation circuitry.

11. The neuromodulation system of claim 1, wherein the pulse train modulation circuitry is digital modulation circuitry.

12. A neuromodulation system for modulating neural tissue by delivering a modulated electrical pulse train to the neural tissue, the neuromodulation system comprising:

a plurality of electrical terminals configured for being respectively coupled to a plurality of electrodes;
neuromodulation output circuitry configured for outputting an electrical pulse train to the plurality of electrical terminals;
a user interface configured to receive a shape selection from a group of two or more shape selections for a modulation signal that may be selected to define a shape of the modulation signal; and
pulse train modulation circuitry configured to modulate a pulse rate of the electrical pulse train outputted from the neuromodulation output circuitry in accordance with the defined shape of the modulation signal to provide the modulated electrical pulse train.

13. The neuromodulation system of claim 12, wherein the user interface includes a control that allows a user to specify at least one limit of the defined shape of the modulation signal.

14. The neuromodulation system of claim 12, wherein the user interface includes a control that allows a user to specify at least one limit of a period of the modulation signal.

15. The neuromodulation system of claim 12, the electrical pulse train has a plurality of parameters, the user interface is configured to receive at least one parameter selection from the user, wherein the least one parameter is selected from the plurality of parameters, the at least one parameter selection to define at least one parameter of the electrical pulse train to be modulated with the modulation signal that has the defined shape.

16. A method, comprising:
receiving, via a user interface, a user selection of a defined shape selected from a group of preprogrammed shapes; and
modulating neural tissue by delivering a modulated electrical pulse train to the neural tissue, wherein delivering the modulated electrical pulse train to the neural tissue includes delivering an electrical pulse train from neuromodulation output circuitry, and modulating the electrical pulse train delivered from the neuromodulation output circuitry using the user selection of the defined shape to provide the modulated electrical pulse train.

17. The method of claim 16, further comprising receiving, via a control on the user interface, at least one limit for modulating the electrical pulse train.

18. The method of claim 17, wherein the at least one limit includes at least one limit of the defined shape.

19. The method of claim 17, wherein the at least one limit includes at least one limit of a period for modulating the electrical pulse train using the user selection of the defined shape.

20. The method of claim 16, wherein modulating the electrical pulse train using the user selection of the defined shape includes modulating at least one of an amplitude, a pulse rate, or a pulse duration of the electrical pulse train using the user selection of the defined shape.

* * * * *